(12) United States Patent
Palatnik De Sousa

(10) Patent No.: US 10,172,940 B2
(45) Date of Patent: Jan. 8, 2019

(54) PROCESS AND COMPOSITION FOR TREATMENT OF CANINE AND HUMAN LEISHMANIASIS

(75) Inventor: Clarisa B. Palatnik De Sousa, Rio de Janeiro (BR)

(73) Assignee: Universidade Federal do Rio de Janeiro, Rio de Janeiro (BR)

(*) Notice: Subject to any disclaimer, the term of this patent is extended or adjusted under 35 U.S.C. 154(b) by 0 days.

(21) Appl. No.: 13/383,952

(22) PCT Filed: Feb. 3, 2010

(86) PCT No.: PCT/BR2010/000037
§ 371 (c)(1),
(2), (4) Date: Feb. 21, 2012

(87) PCT Pub. No.: WO2011/006219
PCT Pub. Date: Jan. 20, 2011

(65) Prior Publication Data
US 2012/0141535 A1 Jun. 7, 2012

(30) Foreign Application Priority Data

Jul. 13, 2009 (BR) .................................... 0902443

(51) Int. Cl.
*A61K 39/00* (2006.01)
*A61K 45/06* (2006.01)
*A61K 39/008* (2006.01)
*A61K 31/706* (2006.01)

(52) U.S. Cl.
CPC ............ *A61K 45/06* (2013.01); *A61K 31/706* (2013.01); *A61K 39/008* (2013.01); *A61K 2039/55577* (2013.01)

(58) Field of Classification Search
None
See application file for complete search history.

(56) References Cited

FOREIGN PATENT DOCUMENTS

WO WO 2006/122382 11/2006
WO WO 2008/134643 11/2008

OTHER PUBLICATIONS

Borja-Cabrera et al. (Vaccine, 20:3277-3284, 2002).*
Borja-Cabrera et al. (Vaccine 28:597-603, 2010; available online Oct. 1, 2009).*
Borja-Cabrera et al. (Vaccine, 22:2234-2243, 2004).*
Moritz et al. (Tokai J. Exp. Clin. Med., 23:279-283, 1999).*
Bianciardi et al. "The efficacy of enrofloxacin, alone or combined with metronidazole, in the therapy of canine leishmaniasis." Parasitol Res 93, 2004.
International Search Report for PCT Application No. PCT/BR2010/00037, dated Jun. 16, 2010.
Solano-Gallego et al. "Directions for the diagnosis, clinical staging, treatment and prevention of canine leishmaniosis." Veterinary Parasitology 165 (2009) 1-18.
C B Palatnik et al., Inhibition of Leishmania donovani Promastigote Internalization into Murine Macrophages by Chemically Defined Parasite Glycoconjugate Ligands, Infection and Immunity, vol. 57: pp. 754-763 (1989).
Da Silva V et al., A phase III trial of efficacy of the FML-vaccine against canine kala-azar in an endemic area of Brazil (São Gonçalo do Amaranto, RN), Vaccine, vol. 19: pp. (2001) 1082-1092.
Borja Cabrera GP et al., Immunogenicity assay of the Leishmune® vaccine against canine visceral leishmaniasis in Brazil, Vaccine, vol. 26: pp. 4991-4997 (2008).
Nogueira F S et al., Leishmune® vaccine blocks the transmission of canine visceral leishmaniasis Absence of *Leishmania* parasites in blood, skin and lymph nodes of vaccinated exposed dogs, Vaccine, vol. 23(40): pp. 4805-4810 (2005).
Saraiva E et al., The FML-vaccine (Leishmune®) against canine visceral leishmaniasis: A transmission blocking vaccine, Vaccine, vol. 24: p. p 2423-31 (2006).
Palatnik de Sousa C B et al., Decrease of the incidence of human and canine visceral leishmaniasis after dog vaccination with Leishmune® in Brazilian endemic areas, Vaccine, vol. 27: pp. 3505-351 (2009) (Abstract Only).
Santos F N et al., Immunotherapy against experimental canine visceral leishmaniasis with the saponin enriched-Leishmune® vaccine, Vaccine, vol. 25: pp. 6176-6190. (2007).

* cited by examiner

*Primary Examiner* — Brian Gangle
(74) *Attorney, Agent, or Firm* — Pearl Cohen Zedek Latzer Baratz LLP

(57) ABSTRACT

Process and immune chemotherapeutic/pharmaceutical composition for treatment of canine and human Leishmaniasis comprising a vaccine containing the FML antigen (Fucose Mannose-Ligand) and saponin adjuvant, used in association with chemotherapeutic agents, showing healing property, leaving the dogs previously infected, in the condition of sterile cure of visceral and tegumentary leishmaniasis, characterized by absence of parasites and the overall absence of *Leishmania* DNA, aiming to stave off the spread of the parasite which causes canine visceral leishmaniasis in dog to the insect transmitter, thus to other dogs and humans. The invention also comprises also the use of the aforementioned composition to produce formulations designed to treat canine visceral leishmaniasis and visceral and murine tegumentary leishmaniasis, human and canine, as well as a kit comprising immune chemotherapeutic agents to treat the same diseases.

18 Claims, 3 Drawing Sheets

PROCESS AND COMPOSITION FOR TREATMENT OF CANINE AND HUMAN LEISHMANIASIS

CROSS-REFERENCE TO RELATED APPLICATIONS

This application is a National Phase Application of PCT International Patent Application No. PCT/BR2010/000037, International Filing Date Feb. 3, 2010, claiming priority of Brazilian Patent Application No. PI 0902443-3, filed Jul. 13, 2009, which is hereby incorporated by reference in their entirety.

FIELD OF THE INVENTION

The present invention relates to a process and compositions for treatment of canine and human visceral leishmaniasis comprising immune-therapeutic agents used in combination with conventional chemotherapeutic agents. These immune-chemotherapeutic agents include fractions of promastigotes or amastigotes of *Leishmania* called "Fucose Mannose Ligand" (FML) adjuvanted with saponin, in combination with chemotherapy. The chemotherapeutic agents include antibacterial antibiotics, antiparasitic and/or antifungal and/or antiviral and/or analogues of nucleotides or nucleosides.

Such processes and compositions may be employed in the preparation of formulations used to treat leishmaniasis in both animals and humans.

BACKGROUND OF THE INVENTION

The visceral human leishmaniasis or "kala-azar" in the Americas and the Mediterranean is a known canine zoonosis. Blood-sucking insects acquire the etiologic agent by feeding themselves from wild canids and subsequently transmitting it to domestic dogs. Transmission to humans by sandflies causes visceral human leishmaniasis, a serious disease that can be fatal if not treated properly.

Roughly 500,000 new human cases of kala-azar are reported annually worldwide. A protective prophylactic vaccine against human disease is not yet available. The best performance to date has been achieved with an experimental first-generation vaccine that induced 12% protection among people who converted to positive in an intradermal test for the lysate of *Leishmania* (IDR) after vaccination is completed. Thus far, chemotherapy against kala-azar has proved to be highly toxic and not always effective.

*Leishmania* (L.) *chagasi* and *Leishmania* (L.) *infantum* are the etiological agents of human visceral leishmaniasis (HVL) in America, in the Mediterranean, Middle East and Asia. It is a severe and often lethal disease if not treated soon after onset of symptoms. In these regions, the disease is a canine zoonosis. The parasites are exposed on the skin of dogs, foxes, and wild dogs, and are transmitted to humans via a transmission cycle involving insects and sandflies.

Zoonotic Visceral Leishmaniasis (ZVL) is a re-emerging canine zoonosis, whose epidemiological control involves the slaughter of seropositive-infected dogs, treatment of domestic and peridomestic environments with insecticide, and systematic the treatment of human cases. Brazil is one of the four countries where 90% of the human cases occur. As a control method, the slaughter of seropositive dogs is practiced in Brazil and China; however, it is not accepted in Europe. The canine control programs are extremely difficult, costly, and require permanent surveillance and sensitive serological diagnostic methods to be effective. Furthermore, as many seropositive dogs are asymptomatic, the campaign is complicated, although the infectiousness of asymptomatic dogs for vector insects has been demonstrated.

Treatment of homes with insecticides and preventive vaccination of humans and dogs against visceral leishmaniasis are presently regarded as the best tools provided for control and eradication of the disease and reduce both the human and canine cases. Although several vaccines have been tested under experimental conditions, only some showed efficacy in field tests against the challenge of natural infection, and only Leishmune® vaccine is currently licensed in Brazil, as a prophylactic vaccine against canine visceral leishmaniasis.

DETAILED DESCRIPTION OF THE INVENTION

The Leishmune® vaccine is comprised of the FML (Fucose Mannose Ligand) antigen from *Leishmania donovani* formulated in 0.5 mg of saponin. The isolation of the FML antigen from *L. donovani* promastigotes (C B Palatnik et al., Infection and Immunity 1989; 57:754-763) and its formulation as a vaccine with saponin of *Quillaja saponaria* Molina is described in Brazilian patent PI1100173-9.

The vaccine composed of with FML antigen and saponin protected 92-95% of dogs yielding 76-80% of vaccine efficacy in trials carried out in Rio Grande do Norte (da Silva V et al., Vaccine 2001; 19:1082-1092; 2001, and Borja Cabrera G P et al., Vaccine 2002; 20: 3277-3284, 2002). Leishmune® has already demonstrated 99% protection of vaccinated dogs in Sao Paulo and Minas Gerais, while 15.6% of untreated controls were seropositive (Borja Cabrera G P et al., Vaccine 2008 26:4991-4997). In a two-year field trial, up to 1.2% of the vaccinated dogs showed symptoms while 20.6% of dogs exposed controls were symptomatic. Finally, while 1% of the deaths were due to visceral leishmaniasis were detected amongst the vaccinates, a total of 39% of control animals died of CVL during the trial. All differences between vaccinated and controls were significant. These results demonstrate 99%-protection in vaccinated animals with Leishmune®.

Figure 1:
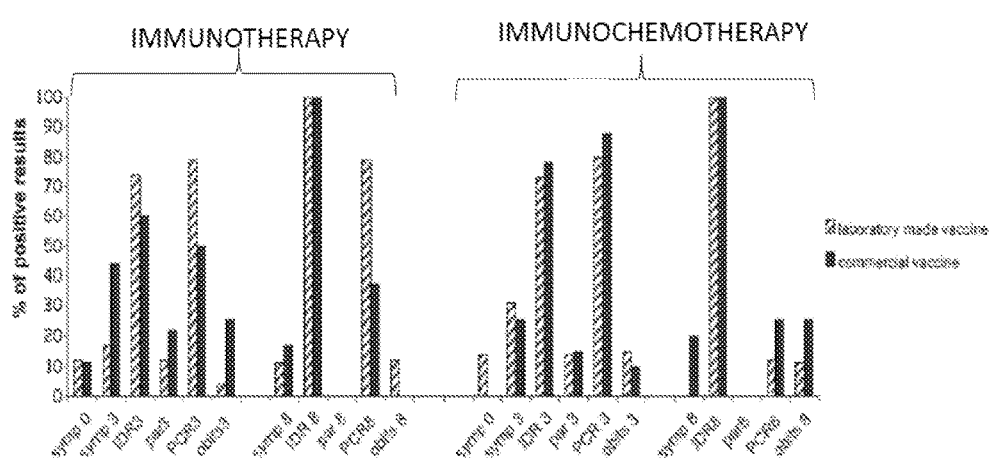
FIG. 1 is a comparative analysis of the impact of the laboratory-made and the commercial Leishmune®-enriched vaccines on the proportions of symptomatic cases (symp), obits, parasite (par) and PCR evidence in lymph nodes and MR to *Leishmania* antigen, when used either in immunotherapy or immunochemotherapy against CVL.

FIG. 1 is a comparative analysis of the impact of the laboratory-made and the commercial Leishmune®-enriched vaccines on the proportions of symptomatic cases (symp), obits, parasite (par) and PCR evidence in lymph nodes and IDR to *Leishmania* antigen, when used either in immunotherapy or immunochemotherapy against CVL. The numbers 3 and 8, after the variable names on horizontal axis indicate months after vaccination. The immunotherapy treatment group was composed of 15 dogs that received the commercial and 16 dogs that received the laboratory-made vaccine while the immunochemotherapy treatment was given to 21 dogs treated with the commercial vaccine and 14 dogs treated with the laboratory-made enriched-Leishmune® vaccine. No significant differences between the laboratory-made or the commercial formulations were found in the proportion of positive results of any variable neither in the IT nor in the ICT treatment. Comparison of proportions was done using the Fisher exact test (Graphpad Software).

The Leishmune® vaccinated dogs did show skin parasites, have an absence of positive PCR tests on blood and lymph nodes and immunohistochemistry of skin, and thus result in a lessening of infection of vector insects (Nogueira F S et al., Vaccine 2005; 23(40):4805-4810). Also, the antibodies in vaccinated dogs hamper the spread of the disease by inhibiting potential parasites present in the sucked blood from interacting with the intestinal membrane of the insect thus preventing the normal development of its cycle and the future infection of new humans or dogs (Saraiva E et al., Vaccine 2006; 24: 2423-31). Thus, sand flies fed with sera from infected dogs (anti-FML antibodies IgG1 predominant) showed a distinct increase of infection (230.7%), while insects fed with serum from dogs vaccinated with Leishmune® (IgG2 antibodies predominant anti-FML) showed 74.3% reduction of infection. These results indicate that Leishmune® is a Transmission-Blocking Vaccine (TBV), and that the antibodies present in serum from vaccinated dogs, even 12 months after vaccination, assist in stopping the continued spread of the disease.

Although the current vaccine coverage in Brazil is still low, a clear decline in number of human and canine cases in the localities where vaccinations took place has been noticed while an increase of cases is detected in the regions where vaccination is not being done (Palatnik de Sousa C B et al., 2009; Vaccine 27:3505-3512).

The possible additive effect of canine vaccination with Leishmune® coupled with the destruction of infected dogs in the reduction of the epidemic was investigated. In Belo Horizonte (BH), rising curves of canine and human incidence were noticed in the counties of Barreiro, Venda Nova and Noroeste, while human and canine incidence of Centro Sul, Leste, Nordeste, Norte, Pampulha and Oeste, showed decline or remained stable after vaccination with Leishmune®. As shown in Table #1, among the counties showing a decline in the percentage of human incidence (−36.5%), Centro Sul and Pampulha showed the highest percentages of dog vaccination (63.27% and 27.27% respectively) and the lowest canine incidences (−3.36%, 1.89%, respectively).

They were followed by Oeste, which vaccinated 25.30% of the animals and experienced an increase of 12.86% of the canine incidence and by Leste and Nordeste with lower proportions of vaccines (11.72 and 10.76%, respectively) and probably for this reason, slightly higher canine incidences (42.77 and 35.73%). The only exception was found in Norte district, where the drop of human and canine incidence not correlate with the vaccination with Leishmune® (Palatnik de Sousa C B et al., 2009; Vaccine 27:3505-3512).

Much smaller proportions of dogs were vaccinated in Venda Nova (4.35%), Noroeste (10.27%) and Barreiro (0.09%) districts which, according to that, showed very increased canine incidences (24.48, 21.85 and 328.57%, respectively), and pronounced increases in human incidence (14.4 and 17% respectively). The decrease of canine ($p=-0.008$) and human incidences ($p=-0.048$) is directly correlated to the increase of the number of vaccinated dogs, confirming the additive control effect of vaccination with Leishmune® over dog culling, reducing the reservoir of parasites, protecting dogs and, in this way, reducing the risk of transmission of VL to humans and becoming a new effective tool for controlling VL. It was also shown that vaccination with Leishmune® does not interfere in the serological control campaign (110,000 dogs). Only 1.3% positive cases (76 of 5,860) detected among dogs vaccinated with Leishmune® (Palatnik de Sousa C B et al., 2009; Vaccine 27:3505-3512).

TABLE 1

Distribution of canine and human incidence of visceral leishmaniasis and number of Leishmune ® vaccinated dogs in Belo Horizonte in the period 2004-2006.

| Districts | Year | Total dogs | Positive dogs | dog incidence(%) | Δ dog incidence | Cumulative L ® vaccinees | Cumulative % vaccinated dogs | Human cases | Δ human cases (%) |
|---|---|---|---|---|---|---|---|---|---|
| Centro Sul | 2004 | 5190 | 201 | 3.87 | | 1900 | | 5 | |
| | 2005 | 10298 | 274 | 2.66 | | 3686 | | 6 | |
| | 2006 | 6823 | 255 | 3.74 | −3.36 | 4317 | 63.27 | 3 | −40 |
| Leste | 2004 | 12337 | 811 | 6.57 | | 389 | | 16 | |
| | 2005 | 16925 | 1039 | 6.14 | | 768 | | 12 | |
| | 2006 | 8103 | 760 | 9.38 | 42.77 | 950 | 11.72 | 6 | −63 |
| Nordeste | 2004 | 12151 | 1044 | 8.59 | | 374 | | 24 | |
| | 2005 | 18684 | 1544 | 8.26 | | 851 | | 14 | |
| | 2006 | 10792 | 1258 | 11.66 | 35.73 | 1161 | 10.76 | 18 | −25 |
| Norte | 2004 | 11551 | 1014 | 8.78 | | 27 | | 22 | |
| | 2005 | 20817 | 2295 | 11.02 | | 46 | | 20 | |
| | 2006 | 12190 | 1203 | 9.87 | 12.41 | 49 | 0.40 | 13 | −41 |
| Pampulha | 2004 | 3899 | 372 | 9.54 | | 824 | | 6 | |
| | 2005 | 11998 | 1082 | 9.02 | | 1741 | | 10 | |
| | 2006 | 7993 | 777 | 9.72 | 1.89 | 2180 | 27.27 | 3 | −50 |
| Oeste | 2004 | 6116 | 456 | 7.46 | | 652 | | 10 | |
| | 2005 | 11799 | 850 | 7.20 | | 1338 | | 11 | |
| | 2006 | 6484 | 546 | 8.42 | 12.86 | 1641 | 25.30 | 10 | 0 |

TABLE 1-continued

Distribution of canine and human incidence of visceral leishmaniasis and number of Leishmune ® vaccinated dogs in Belo Horizonte in the period 2004-2006.

| Districts | Year | Total dogs | Positive dogs | dog incidence(%) | Δ dog incidence | Cumulative L ® vaccinees | Cumulative % vaccinated dogs | Human cases | Δ human cases (%) |
|---|---|---|---|---|---|---|---|---|---|
| Average/year | | 11027.89 | 882.83 | 7.88 | 17.05 | 1271.89 | 23.12 | 11.94 | −36.5 |
| Barreiro | 2004 | 8783 | 197 | 2.24 | | 2 | | 6 | |
| | 2005 | 7609 | 375 | 4.93 | | 4 | | 6 | |
| | 2006 | 6434 | 617 | 9.6 | 328.57 | 6 | 0.09 | 7 | 17 |
| Venda | 2004 | 11434 | 1177 | 10.29 | | 134 | | 21 | |
| Nova | 2005 | 19378 | 2263 | 11.68 | | 259 | | 14 | |
| | 2006 | 12072 | 1547 | 12.81 | 24.48 | 525 | 4.35 | 24 | 14 |
| Noroeste | 2004 | 9021 | 760 | 8.42 | | 375 | | 24 | |
| | 2005 | 17127 | 1516 | 8.85 | | 1000 | | 17 | |
| | 2006 | 11572 | 1187 | 10.26 | 21.85 | 1188 | 10.27 | 25 | 4 |
| Average/year | | 11926.33 | 1113.56 | 8.94 | 124.97 | 388.11 | 4.90 | 16 | 11.67 |
| CI95% | | 5698.73−18153.93 | 215.74−2011.37 | 6.55−11.33 | −119.45−369.39 | 82.35−693.87 | −2.18−11.98 | 4.82−27.18 | 2.23−21.11 |

Legend to Table 1: dog incidence (%): percent of seropositive dogs among the total dogs; Δ dog incidence: variation on percentual of dog incidence in 2006 in relation to 2004; cumulative L ® vaccinees = cumulative number of Leishmune ® vaccinated dogs that receive complete vaccination (3 doses in the first year and one annual booster in the following years) distributed to the veterinarians; Cumulative % of vaccinated dogs: percentual variation of the number of vaccinated dogs in 2006 relative to 2004; Δ human cases: percentual variation of the number of human cases in 2006 in relation to 2004. IC95% = 95% confidence interval.

Considering that infected dogs are slaughtered and that the vaccine is prophylactic and blocks the transmission of the disease, the increase in saponin adjuvant concentration converts the vaccine into a therapeutic composition, offering a future alternative to the slaughter of dogs. It was indeed found that Leishmune® vaccine formulated with a double concentration of saponin (1 mg/dose) had therapeutic effect both against experimental canine visceral leishmaniasis (Santos F N et al., Vaccine 2007; 25: 6176-6190) and against the naturally acquired infection in the endemic area (Borja Cabrera G P et al., Vaccine 2004; 22: 2234-2243). The immunotherapy with saponin-enriched Leishmune® vaccine increased levels of IgG2 antibodies correlated with protective response, the levels of CD8+ lymphocytes producers of gamma interferon, and yielded from 79 to 95% of positive IDR responses, resulting in the survival of dogs treated for up to 5 years (to date) which showed no symptoms and which were free of parasites in the 22$^{nd}$ month of the experiment. By the same date, 37% (17/46 dogs) of deaths by CVL were recorded in the untreated control group (Borja Cabrera G P et al., Vaccine 2004; 22: 2234-2243).

The immunotherapy with Leishmune® represents a benefit in the treatment of the dogs, where the chemotherapy treatment is not recommended or forbidden, such as in Brazil. The concern is that the use of few available human drugs might select resistant parasites. Also controversial efficacy results were found in after dog chemotherapy against CVL. In fact, despite generating a temporary remission of symptoms, relapse usually takes place weeks or months after the completion of treatment. VL in humans is often treated with Meglumine antimoniate (Glucantime®) allopurinol, Amphotericin B or the combination of Glucantime and allopurinol.

The present invention surprisingly discloses that chemotherapy combined with immunotherapy with the enriched Leishmune® vaccine of saponin enables eradication of the disease in dogs with canine visceral leishmaniasis, not only by their increase in survival but also by the absence of parasites and parasite-DNA in them.

As an illustration, however not limited, the following chemotherapy agents can be effectively utilized in combination with a vaccine in the compositions and methods of the present invention: analogs of inosine, formicine and analogues of nucleosides; antibacterial antibiotics: aminoglycosides, amphenicols, ansamycins, beta-lactams such as penicillin and cephalexins lincosamides, macrolides, polypeptides, tetracyclines, cycloserine, mupirocin, tuberines, diaminopyrimidines, nitrofurans, quinolones, sulfonamides, sulfones, enrofloxacin, paromomycin and other aminoglycosides, antiparasitic drugs: allopurinol, pentavalent antimonials (N-Methyl-meglumine, Na stibogluconate), amphotericin B, liposomal amphotericin B, aminosidine, pentamidine, alkylphosphocholines, metronidazole, buparvaquone, sitamaquine or 8 aminoquinoline and temporins, anti-fungal drugs such as: ketoconazole, fluconazole, itraconazole, terbinafine, and anti-cancer drugs such as the miltefosine and stimaquine among others.

In the present invention, both in the Composition as well as in the Formulation, Use or Kit, the saponin, preferably, is enriched. The invention will be better understood from the following illustrative trial:

A total of 104 dogs with canine visceral leishmaniasis from the state of Sao Paulo, Brazil were assessed in this trial. All of the cities showed recent epidemic episodes of canine and human VL. All animals were seropositive to FML antigen of Leishmania (L.) donovani in the FML-ELISA trial and asymptomatic at the start in the trial. All dogs were regularly monitored by two Veterinary Clinics.

In order to avoid any interference in the trial and knowing that the increase in anti-FML serum antibodies of infected dogs is related to the increase in the number of symptoms and to the positive Leishmania DNA-PCR results, the distribution of dogs in the treated group followed a stratified randomization according to serum absorbance values in the FML-ELISA assays. In this experiment the IT and ICT treated groups showed similar composition of breeds (Table #2), and thus each group had no meaningful differences in the proportions of breeds of dogs having greater susceptibility to CVL. Three doses of vaccine were injected via the subcutaneous route in the back of the animals, with a 20-to-30-day interval.

TABLE 2

Breed composition after randomization of IT and ICT groups.

| Immunotherapy | Number of Dogs | Immune Chemotherapy | Number of Dogs |
|---|---|---|---|
| German Shepherd* | 1 | German Shepherd | 1 |
| Doberman* | 1 | Doberman* | 1 |
| Boxer* | 4 | Boxer* | 3 |
| Schnauzer* | 1 | Cocker Spaniel* | 1 |
| Australian Shepherd | 2 | Rottweiler * | 4 |
| Pit Bull | 2 | Poodle | 4 |
| Poodle | 2 | Labrador | 2 |
| Labrador | 4 | Pit Bull | 1 |
| Pinscher | 1 | Pinscher | 2 |
| Daschund | 1 | Brazilian Terrier | 3 |
| Lhasa Apso | 1 | Daschund | 4 |
| Basset hound | 1 | Dogo | 1 |
| SRD | 10 | SRD | 8 |
| Total | 31 | | 35 |

The breeds indicated by * are considered susceptible to CVL by clinical, parasitological or genetic criteria.

Initially, dogs treated with the saponin-enriched Leishmune® vaccine (1 mg) were compared with dogs treated with the same vaccine developed in the laboratory with the results showing that there were no significant differences between the percentage of symptomatic dogs, or of dogs with positive IDR or PCR reactions or parasites in lymph nodes and deaths by CVL, indicating that the commercial Leishmune® formulation has the same immunotherapeutic properties as the laboratory formulation (FIG. 1).

Considering the above results, the dogs vaccinated with the commercial Leishmune® vaccine or with the laboratory vaccine were assessed together. Subsequently, the immunotherapy effect (IT) of the Leishmune® vaccine (n=31) was compared to the immunechemotherapeutic effect (ICT) (n=35), using the Leishmune® saponin-enriched vaccine along with allopurinol (10-20 mg/kg, preferentially 10 mg/kg every 12 hours for 15 months in 23 dogs) or allopurinol in combination with amphotericin B, (0.5 mg/kg, every three days, 16 doses in 9 dogs) in the treatment against CVL and enrofloxacin (5 mg/kg once a day, for 10 days in 1 dog) or cephalexin (30 mg/kg every 12 hours, for 7 days in 1 dog) against secondary infections.

No meaningful difference in the proportion of symptomatic dogs was found among non-treated controls, IT or ICT treated dogs prior to treatment (month 0) (Picture #2) confirming the homogeneity of the groups.

Figure 2:
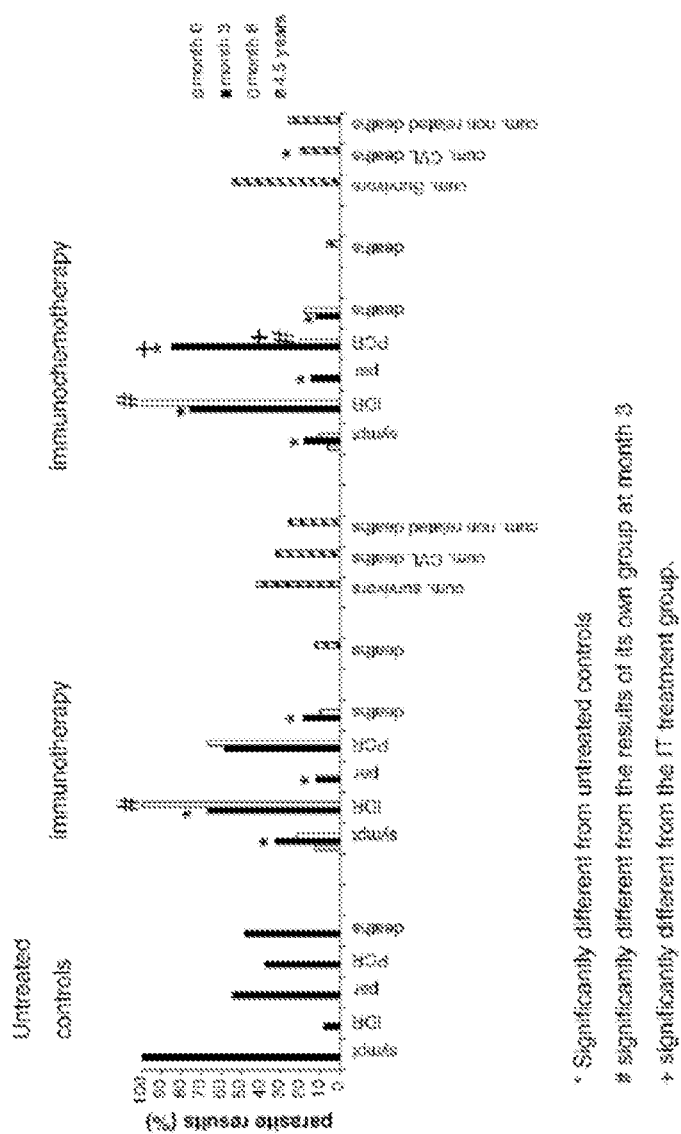
FIG. 2 is a clinical, parasitological and immunological sings in dogs with CVL, after treatment with the saponin enriched-Leishmune® vaccine with or without additional chemotherapy.

FIG. 2 is a clinical, parasitological and immunological sings in dogs with CVL, after treatment with the saponin enriched-Leishmune® vaccine with or without additional chemotherapy. Thirty-one dogs with naturally acquired CVL received three doses of saponin enriched-Leishmune® only (IT), 35 were treated with the vaccine and additional chemotherapy (ICT) while 25 remained as untreated controls. The CVL characteristic signs were evaluated on months 0, 3 and 8 after the first vaccination doses. The proportion of obits, positive findings of Leishmania amastigotes or Leishmania DNA amplified by PCR in lymph nodes, and the proportion of IDR positive responses to leishmanial promastigote antigen were also recorded at months 3 and 8. The bars represent the proportion of positive results in each group of treatments. Comparison of proportions was done using the Fisher exact test (Graphpad Software).

In the third month after vaccination (FIG. 2), similar efficacy and no considerable differences were found between the two treatments in most variables. When compared with untreated controls, both IT and ICT treatments have increased positive IDR-response ratio (from 8 to 67-76%) and reduced the ratio of symptomatic cases (from 100 to 33-18%) the ratio of cases with evidence of parasites (from 54 to 12-15%), and deaths ratio attributable to CVL (from 48 to 19-12%) revealing the control of clinical and parasitological disease that results in the majority of dogs becoming asymptomatic. Until month 3 however, neither IT or ICT treatments were able to eliminate the evidence of leishmania DNA in lymph nodes and even a significant increase in PCR positivity over the untreated controls (38%; p=0.0075) and over the IT group (58%; p=0.0487), was seen in dogs of the ICT group (85%), indicating their important Leishmania latent infection condition (FIG. 2). The result points out that both treatments—IT and ICT—, soon after vaccination, increased and maintained the protective cellular immune response against Leishmania infection, fending off the spread of the disease, reducing the deaths ratio and turning dogs asymptomatic. However, latent infection by Leishmania is revealed by the presence of residual Leishmania DNA detected by molecular diagnostic tools. Therefore the recovery of the cellular immune response is due to the IT treatment with Leishmune® since no significant additional contribution of the chemotherapy treatment is observed on this variable.

As the potential therapeutic effects of Leishmune® vaccine enriched through IT and ICT was evident by the third month, and symptoms and death were significantly increased in untreated controls, for ethical reasons, veterinarians, in this trial, decided to treat the control dogs with chemotherapy against CVL and they were omitted out from the study after treatment.

FIG. 2 also presents the results obtained on month 8 after vaccination was completed. Dogs of both IT and ICT groups showed further increases in the proportions of positive results of IDR, present in only 8% of the untreated controls on month 3, and detected in 100% of animals on month 8. These results represent 33 to 24% of respective meaningful increase on the scores recorded on month 3, showing that all infected dogs recovered their active cellular immune response against Leishmania subsequent to vaccination. No significant change in the symptomatic cases, deaths, or evidence of parasite was noticed, indicating that both treatments result in an asymptomatic condition by month 3. The only major difference noticed between the two treatments on month 8 was a sharp decline in the ratio of dogs showing positive PCR results (from 85 to 20%; p=0.0001), observed only in the ICT group, while the IT group remained unchanged (from 58 to 67%, p=0.7288), suggesting that the chemotherapy treatment added to vaccination with Leishmune enriched with saponin cleared latent infection, therefore healing the dogs. A highly meaningful difference between the positivity on PCR from the ICT group (20%) and from IT group (67%) on month 8 (p=0.0253) (FIG. 2) point out that 70% of the increase in the healing rate was achieved by ICT treatment.

Information obtained 4.5 years after the outset of the trials showed no significant difference in survival rate of IT or ICT group, with only 13% of dogs in the IT group (3/23) and 7% of the ICT group (2/30) dying of CVL between month 8 and 4.5 years (FIG. 2). The cumulative-deaths ratio by CVL within 4.5 years of experiment was 32% for the IT group (10/31) and 20% of the ICT group (7/35) (p=0.2780). This not significant difference suggests a similar healing rate by the two treatments. However, and most surprisingly, when compared with the untreated control group on month 3 (12/25 dogs, 48%), a reduction in the deaths rate by CVL is experienced only after treatment by ICT (7/35 dogs, 20%, 0.0273), but not after IT treatment (32%, p=0,278) (FIG. 2). Regarded together with the negative results of PCR of lymph nodes, the results indicate the advantage of the ICT treatment for control and cure of CVL.

For dog owners and veterinarians, the success of the chemotherapy means the remission of clinical signs, but in endemic areas this is unacceptable because the vectors are still present and the likelihood that these dogs are still infectious and that the disease might be transmitted to humans cannot be ruled out. For parasitologists, a cure means the riddance of parasites, while for public health agencies, epidemiologists and entomologists, the lack of infectivity for blood-feeding sandflies and transmission-blockage of resistant strains, is sufficient. However, the clinical and parasitological cure is insufficient to consider the animal as "cured" since a sterile cure would mean that there is no evidence of parasites or Leishmania DNA in the animal and that it is no longer able to transmit the disease.

The treatment of dogs infected with enriched Leishmune® is able to enhance the cellular immune response, reduce the symptoms, including the presence of parasites in lymph nodes, and deaths. That is, the treatment of IT with enriched Leishmune® is able to control the disease, induce remission, and promote a fast clinical and parasitological cure of animals. In the ICT treatment, the further use of chemotherapy can achieve, 8 months after the outset of vaccination, the healing of animals, including clearance of Leishmania DNA from the lymph nodes, as shown by methods of high-sensitivity molecular diagnosis, leaving the dogs not infectious. Indeed, these animals no longer present a risk of disease transmission to humans in endemic areas. The finding of a lower cumulative index of deaths in the group treated by ICT, 4.5 years subsequent to the onset of the experiment, indicates the superiority of this treatment.

The results of this invention, investigated in groups of 31 to 35 dogs, is more significant when compared with other literature studies which utilize only 5 to 17 dogs.

Using only chemotherapy with pentavalent antimony, allopurinol, amphotericin B, liposomal amphotericin B, aminosidine, pentamidine or an assortment of antimicrobial and antifungal drugs such as metronidazole, ketoconazole and fluconazole induces some clinical improvement, but the parasitological cure is rarely found and DNA evidence usually persists.

In fact, after treatment with antimoniate, parasites were recovered from 79% of the 15 dogs treated and 5/6 dogs were PCR positive. Even 9/10 of the dogs treated with allopurinol showed clinical recovery but 8 of them were positive for parasites in culture of parasites or PCR removed from lymph node. Furthermore, 5 of 6 dogs treated with meglumine and allopurinol remained positive in the parasitological aspect and 2 of them were infectious for phlebotomy. Thirteen dogs were treated with liposomal amphotericin B showed fast clinical improvement, albeit remained positive in the parasitological aspect, and recurrence was detected in 12 of them. Eleven out of 12 dogs, treated with aminosidine improved clinically, but 4/4 showed parasites in culture samples of lymph nodes. With higher doses of aminosidine 3/12 dogs showed absence of symptoms and parasites for 4 years with relapse occurring in 9 others. Dogs treated with pentamidine also improve clinically, but show recurrence of the disease.

Immunotherapy with the saponin-enriched Leishmune® vaccine achieved better results than those previously reported for chemotherapy alone, and that immunochemotherapy with Leishmune® was better than the treatment with immunotherapy alone.

The immunochemotherapy with the enriched Leishmune® is better than the usual chemotherapy with allopurinol, provided that it cuts down the time allocated and the intrinsic toxicity. While dogs treated with allopurinol only recover from 2 to 6 months, without parasitological cure or negative results for PCR even with 20 months of treatment and relapse in % dogs, treatment by ICT with Leishmune® and 15 months of allopurinol showed 89%-clinical cure, 100% parasitological cure and recovery of the cellular immune response, and 76% of negative PCR by month 8.

The ICT effect has been studied for a vaccine of Leishmania (L.) infantum lysate and Glucantime® in 5 dogs monitored for six (6) months. Treated animals showed clinical improvement, but recurrence in 3/5 months and positive lymph nodes. Thus, immunotherapy with enriched Leishmune® was better than immunochemotherapy with L. infantum vaccine.

It was recently noticed that immunotherapy with Leishmune®, (containing 0.5 mg of saponin) using two simultaneous doses, left infected dogs asymptomatic and negative for immunohistochemistry for 2 years.

Bearing in mind the deficiencies of chemotherapy in CVL and its negative impact on epidemiological control of the disease, the use of a protective vaccine in immunotherapy of already infected dogs is highly encouraging and would have greater acceptance in the community than control based upon slaughter of infected dogs. This invention demonstrates the therapeutic value of the saponin enriched Leishmune® vaccine in conjunction with chemotherapy, when used in the immunechemotherapeutic treatment canine visceral leishmaniasis, resulting in an effective control of the disease in endemic areas.

The beneficial effect of the therapy or immunochemotherapy with FML-saponin vaccine or Leishmune®, shown in the prevention and treatment of canine visceral leishmaniasis and in the consequent decrease of human visceral leishmaniasis caused by Leishmania chagasi in Brazil can also be utilized to prevent, treat and cure visceral leishmaniasis all over the World. Indeed, the FML antigen isolated from Leishmania (L.) donovani (Sudan), the underlying agent of the human disease in India and some regions of Africa, is recognized by sera of human and dogs infected with L. infantum in Spain (Europe) and by Leishmania chagasi in America (Brazil).

Worldwide, the incidence of visceral leishmaniasis exceeds tegumentary leishmaniasis, a disease more common albeit less lethal, but mutilating in its progression. The FML-saponin vaccine or Leishmune® can thus be used as a tool in the prevention, control, immunotherapy or immunochemotherapy of both visceral and tegumentary leishmaniasis. Of 2,000,000 new annual cases of leishmaniasis in the world, 1,500,000 are tegumentary leishmaniasis, which is a form of three clinical syndromes of variable expression, known as: cutaneous leishmaniasis (CL), mucocutaneous leishmaniasis (MCL) and diffuse leishmaniasis (DL). The species of parasites of the Leishmania genus are separated into two subgenera: Leishmania (L.) and Viannia (V.); there are nearly 30 species that cause morbidity and mortality in endemic areas. While Leishmania from donovani complex (L. (L.) donovani, L. infantum-L. (L.) chagasi) are causative agents of kala-azar or visceral leishmaniasis, the Leishmania mexicana (L. (L.). mexicana, L. (L.). pifanoi, L. (L.) amazonensis, L. enrietti, L. (L.) venezuelensis) and the Leishmania braziliensis complexes (L. (V.) brazilensis, L. (V.) guyanensis, L. (V.) panamensis, L. (V.). peruviana, L. (V.) Lainson, L. (V.) Shaw, L. (V.) Naiffl) cause the cutaneous, mucocutaneous and diffuse Leishmaniasis in the New World while the L. (L.) tropica, L. (L.) major, L (L.) aethiopica are agents of tegumentary leishmaniasis in the Old World.

Figure 3:
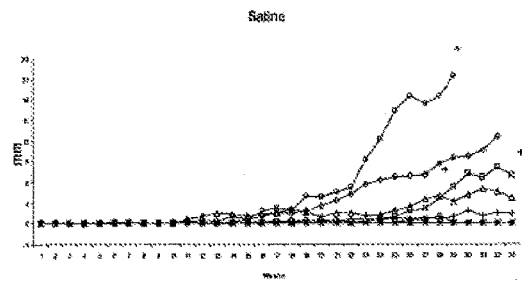
FIG. 3 is the development of the size of the infected paws of BALB/c mice (n=7/group) treated with saline or FML-saponin vaccine and challenged with infective promastigotes of *Leishmania* (L.) *amazonensis*.
Figure 3:
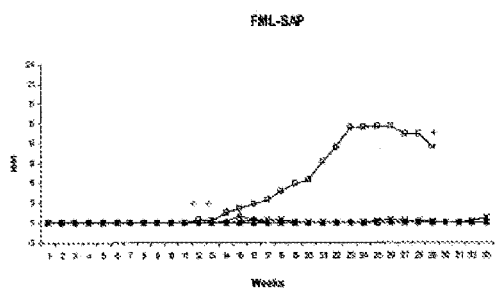

FIG. 3 is the development of the size of the infected paws of BALB/c mice (n=7/group) treated with saline or FML-saponin vaccine and challenged with infective promastigotes of Leishmania (L.) amazonensis.

Figure 4:
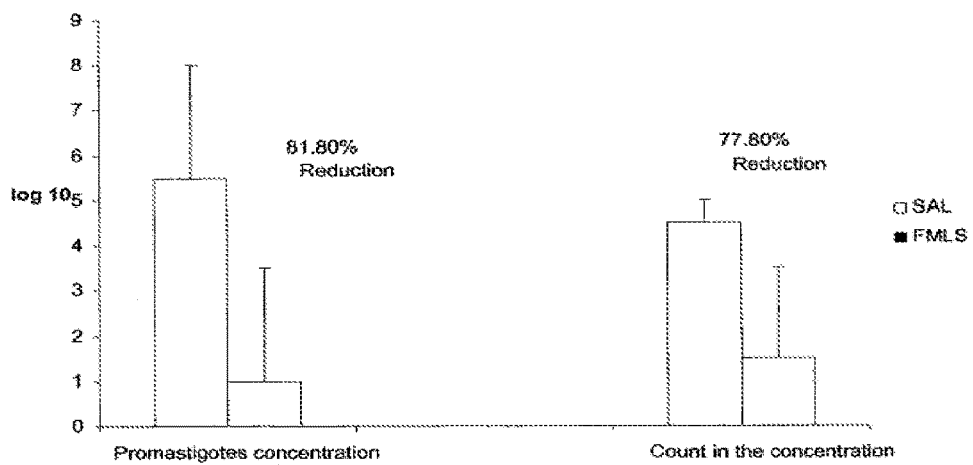
FIG. 4 shows the quantification of parasite load in the paws of mice vaccinated with FML-saponin; left, log 10 of maximum dilution in which parasites are assessed (concentration); right, log 10 number of promastigotes in the dilution equivalent to the concentration.

FIG. 4 shows the quantification of parasite load in the paws of mice vaccinated with FML-saponin; left, log 10 of maximum dilution in which parasites are assessed (concentration); right, log 10 number of promastigotes in the dilution equivalent to the concentration.

Over 90% of the cases of cutaneous leishmaniasis occur in Afghanistan, Iran, Saudi Arabia, Syria, Brazil and Peru.

Experiments demonstrate that the FML-saponin vaccine induced a 65%-protection in mice challenged with L. (L.) mexicana. Also, it has been shown that Balb/c mice vaccinated with 3 doses of FML in conjunction with IL-12, saponin Quil-A, Riedel de Haën or QS-21 induced significantly augmented responses of antibodies and of IDR against lysate of L. (L.) amazonensis. The responses were even greater than those generated in mice vaccinated with the FML analog fraction isolated from L. (L.) amazonensis, confirming the immune prophylactic potential of the FML of L. (L.) donovani against both leishmaniasis. The FML contains as its major antigenic fraction the GP36 glycoprotein, identified after cloning as a Nucleoside hydrolase (NH36) enzyme. This enzyme is vital for the parasite, because it cleaves imported nucleosides releasing the bases used by the parasite for the synthesis its own DNA. A DNA vaccine containing the NH36 Nucleoside hydrolase gene, the VR1012NH36, was prophylactic and immunotherapeutic against murine visceral leishmaniasis by L. (L.) chagasi and murine cutaneous by L. (L.) mexicana, suggesting that this main antigen from FML induces a cross-protection against tegumentary leishmaniasis. Recently, we identified by cloning, the Nucleoside hydrolase of L. (L.) amazonensis with extremely high homology with the identified in L. (L.) donovani, which explains the possible molecular basis of the cross-protection. We also examined the immune response and protection induced in Balb/c mice by vaccination with 3 subcutaneous doses of FML (150 µg)+saponin (100 µg) against infection with $10^6$ promastigotes of L. (L.) amazonensis from amastigotes in hamsters.

On week 26, after infection, meaningful differences were found between the groups, in the increased size of the paws (p=0.004). The FML+saponin vaccine induced a 49%-reduction in the development of the size of the lesions (FIG. 3). Actually, the increase in size of paws was detected in 5 from 7 animals treated with saline and only 1 treated with FML-saponin (FIG. 3). The analysis of parasite load by limiting dilution of injuries tissue of those that survived indicated that there was significant protection in animals vaccinated with FML+saponin (FIG. 4). In fact, an 81.8%-reduction in titers of parasites and a 77.8%-reduction of parasite counts of animals vaccinated with FML-saponin was detected.

The results suggest that the FML-saponin vaccine induces significant cross-protection against tegumentary leishmaniasis by L. (L.) amazonensis and L. (L.) mexicana confirming the potential of this vaccine as a control tool of both visceral and tegumentary leishmaniasis. The previous detection of the immunotherapeutic and prophylactic effect of the DNA vaccine containing the NH36 gene of the FML complex, against canine visceral and murine tegumentary and visceral leishmaniasis, confirms the relevance of the FML complex in protecting against both diseases and suggests its potential healing effect in immunochemotherapy of human visceral and tegumentary leishmaniasis.

What is claimed is:

1. A method of treating a subject infected with Leishmania by clearing Leishmania DNA from lymph nodes of said subject, comprising:
    administering to said subject a composition comprising from 0.5 to 5 mg of Fucose-Mannose Ligand antigen and from 0.5 to 2 mg of saponin adjuvant in combination with administering one or more chemotherapeutic agents for a period of time sufficient to clear Leishmania DNA from lymph nodes of said subject, wherein the one or more chemotherapeutic agents comprise allopurinol, wherein said allopurinol is administered at a dosage of 10-20 mg/kg every 12 hours for 15 months, and wherein said administering said composition comprises administering three doses of said composition with a 20 to 30 day interval between doses.

2. The method of claim 1, wherein said administering said composition is oral, nasal, rectal, vaginal, ocular, intradermal, intraperitoneal, subcutaneous and/or intramuscular administration.

3. The method of claim 1, wherein said subject is a canine or a human.

4. The method of claim 1, wherein said subject suffers from canine visceral leishmaniasis.

5. The method of claim 1 further comprising determining clearance of said Leishmania DNA from said lymph nodes of said subject by a negative result in a molecular diagnosis.

6. The method of claim 5 wherein said molecular diagnosis is polymerase chain reaction (PCR).

7. The method of claim 1 wherein the period of time during which said one or more chemotherapeutic agents is administered is eight months after said vaccination was completed.

8. The method of claim 1 wherein said subject suffers from human or canine leishmaniasis.

9. A method of treating a subject infected with Leishmania by clearing Leishmania DNA from lymph nodes of said subject, comprising:
    administering to said subject a composition comprising from 0.5 to 5 mg of Fucose-Mannose Ligand antigen and from 0.5 to 2 mg of saponin adjuvant, in combination with administering allopurinol at a dosage of 10-20 mg/kg every 12 hours for 15 months, wherein said administering said composition comprises administering three doses of said composition with a 20 to 30 day interval between doses, for a period of time sufficient to clear Leishmania DNA from lymph nodes of said subject.

10. The method of claim 9, wherein said administering said composition is oral, nasal, rectal, vaginal, ocular, intradermal, intraperitoneal, subcutaneous and/or intramuscular administration.

11. The method of claim 9, wherein said subject is a canine or a human.

12. The method of claim 9, wherein said subject suffers from canine visceral leishmaniasis.

13. The method of claim 9, further comprising determining clearance of said Leishmania DNA from said lymph nodes of said subject by a negative result in a molecular diagnosis.

14. The method of claim 13, wherein said molecular diagnosis is polymerase chain reaction (PCR).

15. The method of claim 9, wherein the period of time sufficient to clear said *Leishmania* DNA is eight months after said vaccination was completed.

16. The method of claim 9, wherein said subject suffers from human or canine leishmaniasis.

17. The method of claim 1, wherein said allopurinol is in combination with amphotericin B.

18. The method of claim 9, wherein said allopurinol is in combination with amphotericin B.

* * * * *